(12) United States Patent
Bartolone et al.

(10) Patent No.: US 6,835,210 B1
(45) Date of Patent: Dec. 28, 2004

(54) ELECTROCHEMICAL METHOD AND SYSTEM FOR DYEING HAIR

(75) Inventors: John Brian Bartolone, Bridgeport, CT (US); Padmaja Prem, Saddle Brook, NJ (US); Katherine Jacobs-Dube, Pennington, NJ (US)

(73) Assignee: Unilever Home & Personal Care USA, a division of Conopco, Inc., Chicago, IL (US)

( * ) Notice: Subject to any disclaimer, the term of this patent is extended or adjusted under 35 U.S.C. 154(b) by 0 days.

(21) Appl. No.: 10/712,478

(22) Filed: Nov. 13, 2003

(51) Int. Cl.[7] .................................................. A61K 7/13
(52) U.S. Cl. .................. 8/401; 8/405; 8/406; 8/428; 8/444; 132/207; 132/208; 132/320; 132/321; 132/901
(58) Field of Search ............................ 8/401, 405, 406, 8/428, 444; 132/207, 208, 320, 321, 901

(56) References Cited

U.S. PATENT DOCUMENTS

| | | | |
|---|---|---|---|
| 1,099,062 A | 6/1914 | Laposkey | |
| 1,598,570 A | 8/1926 | Fortenberry | |
| 1,663,078 A | 3/1928 | Harper | |
| 5,072,746 A | 12/1991 | Kantor | 132/219 |
| 5,472,456 A | * 12/1995 | Larsky et al. | 8/405 |
| 5,569,368 A | 10/1996 | Larsky et al. | 204/600 |

FOREIGN PATENT DOCUMENTS

JP 06/315410 10/1996

* cited by examiner

Primary Examiner—Lorna M. Douyon
Assistant Examiner—Eisa Elhilo
(74) Attorney, Agent, or Firm—Michael P. Aronson (57) ABSTRACT

A method for electrochemically dyeing hair is provided which includes first applying to the hair an oxidative dye precursor mixture containing a primary intermediate having a standard Redox potential that is less than about 1V. This precursor mixture on the hair is then contacted with an electrode system that has sufficient voltage to electrochemically oxidize the primary intermediate to produce a colored dye through a coupling reaction. A system or kit is described for carrying out the method.

29 Claims, 2 Drawing Sheets

ELECTROCHEMICAL METHOD AND SYSTEM FOR DYEING HAIR

BACKGROUND OF INVENTION

The present invention is directed at methods and compositions for coloring human and animal hair that do not require the use of chemical oxidants such as peroxides. The method utilizes electrochemical oxidation of certain organic oxidative dye precursors to generate reactive intermediates that can then participate in coupling reactions to form colored molecules capable of dying hair. Specifically, the method comprises applying to the hair an oxidative dye precursor mixture containing at least one primary intermediate and then contacting this mixture on the hair with an electrode system providing sufficient voltage to generate reactive intermediates through oxidation of the primary intermediate. The invention also relates to systems (or kits) that provide the means to accomplish these steps.

Permanent hair colorants commonly come in two parts: a dye solution and a developer solution. The developer solution is generally comprised of an oxidizing agent, typically hydrogen peroxide, and an alkaline buffering agent such as ammonia. In a conventional permanent hair coloring treatment, the dye solution and the developer solution are mixed and then applied to the hair, which is then left for about 25 min to about 45 minutes. The hair is then rinsed with water, treated with a post treatment conditioner, and then rinsed again with water.

The application of a dye solution in combination with an oxidant affords permanent hair coloring. However, as is well known, the repeated use of bleaching agents can damage the hair through indiscriminant oxidation. This is especially important for consumers who either have long hair or who frequently color their hair.

A second problem associated with conventional permanent hair coloring compositions and kits for use at home is inconvenience. Since permanent dyes are generated before they are applied to hair, there is the potential for staining the hands, and face during application and use. This requires gloves, and often masking of areas of the face.

The attainment of natural looking highlights, and tints is another problem encountered with conventional dyeing systems. Although many types of styling implements have been suggested in the art, it remains difficult for the average consumer to approach the aesthetic quality in terms of color nuances that have been heretofore only been available in a salon.

An additional problem associated with conventional dying systems is the convenient "retouching" of the root areas between complete dying as the hair grows. It is often difficult to match the existing color which has changed to varying degrees and consequently consumers may be forced re-dye their hair before it is really necessary.

One objective of the present invention is a method of coloring the hair, especially gray hair that truly does not require a chemical oxidant.

Another objective of the invention is a convenient method of coloring hair that is less messy than conventional dyeing processes and that will provide a wider range of potential shades and tones from a limited set of chemical compositions.

An additional objective of the invention is a method of dyeing the hair that is capable of more easily generating natural looking highlights as well as providing a convenient and effective means of retouching the root area of hair so as to prolong the duration between hair colorings A still further objective is to provide a convenient kit that can be used by individual consumers to practice at home the method described herein.

These and other objectives will become clear from the description of the invention.

The following patents and publications have been considered:

U.S. Pat. Nos. 5,472,456 and 5,569,368, respectively describe a method and system for electrophoretically applying therapeutic and cosmetic agents and dyes especially natural colorant such as melanin, to the hair.

Japanese Patent No. JP 6315410 A discloses a method of dyeing hair by flowing an electric current in an acidic hair dying agent coated on the hair until the agent is oxidized to color the hair. The preferred dyes are acidic inorganic compounds especially pyrogallol.

U.S. Pat. No. 5,072,746 discloses a hair grooming device for the electrocution of lice or other pests on the hair.

None of the references cited above teaches a method of applying to the hair an organic oxidative dye precursor mixture comprising a primary intermediate having a standard oxidation potential between 10 mV and 3 V; and subsequently contacting this mixture on the hair with an electrode system having sufficient voltage to directly form a reactive intermediate that generates an indo dye.

SUMMARY OF THE INVENTION

The subject invention provides a method for dyeing the hair by applying to the hair specific dye precursor compositions and then applying a means for electrochemically oxidizing these precursors to generate colored dye molecules that are substantive to the hair thus avoiding the use of chemical oxidants.

More specifically, the method for electrochemically dyeing the hair comprises carrying out the following steps in the order indicated:

i) applying to the hair an oxidative dye precursor mixture containing at least one primary intermediate having a standard Redox potential less than 1 volt, ii) contacting the oxidative dye precursor mixture on the hair with an electrode system that provides sufficient voltage to electrochemically oxidize at least one of the primary intermediates to produce a reactive intermediate that generates colored dye through a coupling reaction with an oxidative dye precursor present in the mixture, wherein the reactive intermediate is a quinone monoimine, a quinone diimine, a substituted quinone mono- a substituted quinone diimine, an indole imine, a substituted indole imine, or mixtures thereof.

A second embodiment of the invention is a system or kit that allows individual consumers to conveniently practice the disclosed electrochemical method of coloring the hair.

More specifically, the hair coloring system or kit comprises:

i) an oxidative dye precursor mixture containing at least one primary intermediate having a standard oxidation potential between 10 mV and 3 V, iii) an electrode system that provides sufficient voltage to electrochemically oxidize at least one of the primary intermediates to produce a reactive intermediate that generates colored dye molecules through a coupling reaction with an oxidative dye precursor present in the mixture, wherein the reactive intermediate is a quinone monoimine, a quinone diimine, a substituted quinone mono- a substituted quinone diimine, an indole imine, a substituted indole imine, or mixtures thereof.

DETAILED DESCRIPTION OF THE INVENTION

As used herein wt % refers to weight % of an ingredient as compared to the total weight percent of the composition that is being discussed. For example, when wt % is used to discuss the amount of an ingredient that is in the dye precursor mixture, this means weight % as compared to the total weight of the dye precursor mixture.

As used herein "inactive" or "substantially inactive" means that the oxidation hair dye precursors are not chemically reacting or are not chemically reacting to a substantial degree, so as to form coupled or polymerized hair color molecules, or it means that the oxidation hair dye precursors are not chemically reacting in a substantial manner so as to form coupled or polymerized hair color molecules.

Dye precursor mixtures refers generally to those compositions of the present invention which comprise oxidative hair dye precursors and are suitable for use on human hair, e.g., have the appropriate safety profile.

Electrochemical oxidation as used herein, refers to the direct oxidation of an oxidative dye, generally a primary intermediate, by an electron transfer process which occurs at the anode of an electrode system applied to the hair, i.e., an electrolysis process. Thus, an electrode essentially replaces all or part of chemical oxidant as the electron acceptor in the generation of reactive intermediates.

Aligning and distributing means or simply aligning means, refers to the means or implement employed to align the hair and distribute the dye precursor after the dye precursor is applied to the hair.

The present invention relates to methods and compositions for achieving the permanent coloring of hair which methods include two key steps performed in sequence:

1) contacting the hair with a substantially inactive dye precursor mixture of at least one oxidative dye precursor having a standard Redox potential of less than 1 V for a period of about 1 second to about 60 minutes, followed by, 2) applying to the hair an electrode system that provides sufficient voltage to electrochemically oxidize at least one of the primary intermediates to produce a reactive intermediate capable of generating colored indo dye molecules through a coupling reaction with an oxidative dye precursor present in the mixture.

The second step of the above method can be combined with a means of aligning the hair and distributing the precursor mixture to, for example, increases, the effective surface area of hair that is exposed, and distribute the dye precursors more uniformly.

The compositions and methods of the present invention may be used to color different types of hair such as Asian hair and Caucasian hair. It is particularly well suited to coloring gray hair.

While not wishing to be bound by theory or in any way limiting the scope of the invention, the following discussion outlines underlying principles that may be useful in understanding the invention and its preferred embodiments.

As is well known, the first step in the coloring of hair with an oxidative dye involves the generation of a reactive intermediate via an electron transfer reaction. Electron transfer reactions can be induced by using oxidizing agents, e.g., potassium ferricyanide, bleaches like hydrogen peroxide, or by applying a potential sufficient to induce oxidation of the compound at the anode. Organic compounds particularly amines and phenols in general have sufficiently low Redox potentials to allow them to be preferentially oxidized in water by the application of a low voltage, i.e., lower than the voltage required for electrolytic oxidation of water to oxygen.

In the process of electrochemical coloring, preferably at least 50%, more preferably 75% and most preferable at least 90% of the colored dye molecules that are formed, are formed electrochemically and not by chemical oxidation from either a bleach or oxygen present in the air or generated electrochemically.

In a standard electrochemical redox reaction, oxidation occurs at the anode and reduction at the cathode, e.g., Reduction: $A+e^- \rightarrow A^{31}$; and Oxidation: $B \rightarrow B^+ +e^-$ When the reaction inside an electrochemical cell is driven by an external source of current, it is called an electrolytic cell. If dye precursors are kept in contact with an electrochemical source, primary intermediates such as 4-aminophenol (PAP) and 1,4-phenylenediamines (PPD) and their derivatives undergo oxidation. The quinone imine intermediates so formed can readily couple with appropriate "coupler molecule" to generate indo dye without the use of ammonia and peroxide. A reaction scheme describing the mechanism of electrochemical oxidation of PPD and subsequent coupling to 1,3-dihydroxybenzene through a quinone imine intermediate to form an indo dyes is given below based on the studies reported by Klymenko O Y, Giovanelli D, Lawrence N S, Rees N V, Jiang L, Jones T G, and Compton R G in Electroanalysis, 15, 94–960 (2003) herein incorporated by reference.

-continued

Given the above reaction scheme, possible half cell reactions that can occur at the anode are the two oxidation steps involving PDP, and the oxidation of water to oxygen.

| At Anode | |
| --- | --- |
| PPD → PPD$^{\cdot}$ + e$^{-}$ | E° = 0.26 V |
| PPD$^{\cdot}$ → QDI + e$^{-}$ | E° = 0.72 V |
| 4 OH$^{-}$ → O$_2$ (g) + 2 H$_2$O + 4 e$^{-}$ | E° = 0.401 V | where E$^0$ is the standard Redox potential expressed as a reduction potential. In this convention, the smaller (less positive) the value of the Redox potential, the easier the material is to oxidize.

Of these possible reactions, the first reaction (oxidation of PPD) is favored over the formation of oxygen since PPD has a lower Redox potential. Thus, the formation of oxygen at the anode should not take place until the primary intermediate is exhauted.

The standard Redox potentials for PDP and PDP* were taken from *Techniques of Chemistry Vol.5*, Chapter, Techniques of Electroorganic Synthesis Part II, Weinberg, N. L (Editor)—1974–1982.

When the cathode is an inert electrode and the solution being electrolyzed is a simple alkaline aqueous solution of the dyes and inert electrolyte, the reaction that takes place at the cathode during the initial stages of the electrolysis will be the formation of hydrogen.

At Cathode $$2H_2O + 2e^{-} \rightarrow H_2(g) + 2OH^{-} \quad E^0 = -0.83 \text{ V}$$

Thus, for the generation of PPD$^{+*}$ at the anode, a potential difference of −1.09V(−(0.26)+(−0.83)) would be required at standard state. This assumes of course that the standard Redox potential of PPD in water under the pH conditions employed is the same as the potential values quoted above (see below). As the reaction proceeds, however, the reduction of PPD$^{+*}$ and especially QDI becomes a more favored process if appreciable amounts are present in the vicinity of the cathode. This is the case because these reactions involving the reduction of the dye have an overall less negative reduction potential than the generation of hydrogen gas at alkaline pH. This analysis has implications with respect to electrode design that will be discussed further below.

Upon the application of a potential, PPD first undergoes a one-electron loss (oxidation) at the anode to form the radical-cation species PPD$^{+*}$. This species then undergoes a proton exchange with the parent PPD to give the neutral radical species PPD*. The neutral radical species then undergoes further one-electron transfer to form the di-imine. If a coupler molecule is present in solution the di-imine undergoes coupling to form the final indo dye molecule. Of course with other types of primary intermediates other types of reactive intermediates can be formed such as for example, mono-imines, which also participate in coupling reactions leading to acceptable dye molecules.

Thus, if a hair sample is dipped into a coloring formula containing dye precursors and a voltage of about 0.2 to 3V is applied at a pH of 7.0–10.0, respective indo dyes are generated depositing color in the hair.

In the absence of a chemical oxidant, a control sample (no voltage) under identical conditions generates very little color demonstrating that air oxidation is very slow and the observed color formation results from electrochemical oxidation. The rate of color formation in the dye bath is much faster in presence of the applied potential compared to the control (air oxidation). The application of a low voltage electrochemical system will provide sufficient energy to overcome the oxidation potential of the primary intermediates, the critical step in an indo dye formation reaction. Once the primary intermediate is oxidized, subsequent coupling reaction of the QDI with the coupler is very fast and does not require an oxidant.

It should be understood that the above discussion is meant to illustrate the broad principle of the method with but one, albeit preferred, primary intermediate. Obviously there are other chemical species of organic primary intermediates that generate different reactive intermediates and can be used by one skilled in the art and are within the broad scope of the invention and the above discussion is not meant to limit the choice.

It will also be understood by those skilled in the art that concentrations of oxidative hair dye precursors which may be employed in the present invention can be varied depending upon, for example, the hair type which is to be colored and on the coloring effect which is desired.

What follows is a description of the ingredients that can be included in the mixtures and the electrode system providing the means for carrying out the steps of the present invention.

Dye Precursor Mixture

The dye precursor mixture of the present invention includes oxidative hair coloring precursors (called oxidative or oxidation dyes). Such oxidative hair coloring agents are used in combination with an electrode systems of the present invention to deliver color to the hair.

The dye precursor mixture also can contain ingredients used to enhance the solubility of the precursors in a predominantly aqueous medium ("solubility enhancers"). The mixture can also contain agents to control the pH so as to provide an optimal chemical environment for the precursors to interact with hair fibers ("pH control agents").

Oxidative dyes

Permanent hair dye compositions as defined herein are compositions, which once applied to the hair, are substantially resistant to washout and abrasion.

The dye forming intermediates used in oxidative dyes can be aromatic diamines, naphthols, aminophenols and their derivatives. These dye forming intermediates can be classified as; primary intermediates, and couplers (often also referred to as either secondary intermediates or modifiers). As used herein the term "precursor" means precursor, coupler, modifier, or intermediate and the like. Primary intermediates are chemical compounds, which by themselves will form a dye upon oxidation. The coupler or secondary intermediate is used with other intermediates for specific color effects or to stabilize the color.

At least two types of oxidative dyes can be used in the invention: one type is a primary intermediate while the other type is a coupler.

Primary intermediates which are suitable for use in the compositions and processes herein include aromatic diamines, naphthols, polyhydric phenols, aminophenols and derivatives of these aromatic compounds (e.g., N-substituted and/or C-substituted derivatives of the amines, O-substituted and/or C-substituted derivatives of phenols).

Primary oxidation dye intermediates are generally colorless molecules prior to oxidation. Color is generated when the primary intermediate is 'activated' to form reactive intermediates that subsequently join with a coupler, which is also generally colorless, to form a colored, conjugated molecule. In general terms, oxidation hair dye precursors or intermediates include those monomeric materials which, on oxidation, form oligomers or polymers having extended conjugation systems of electrons in their molecular structure.

Because of the new electronic structure, the resultant oligomers and polymers exhibit a shift in their electronic spectra to the visible range and appear colored. For example, oxidation dye precursors capable of forming colored polymers include materials such as p-phenylenediamine, which has two functional groups, and are capable of oxidative polymerization to yield higher molecular weight colored materials having extended conjugated electron systems.

Preferred primary intermediates have a standard Redox potential less that 1V, preferably less than 0.6V and most preferably less than 0.4V. The standards oxidation potentials can be measured by the methods reported in *Techniques of Chemistry Vol.5*, Chapter, Techniques of Electroorganic Synthesis Part II, Weinberg, N. L (Editor)—1974–1982.

A partial list of standard oxidation potentials of several common oxidative dyes that have been reported in the literature is given in Table 1 below. However, these reported Redox potentials were measured in acetonitrile using a platinum electrode and provide only an estimate of the actual oxidation potentials of dyes in an aqueous solution at an alkaline pH. The Redox potentials of several useful primary intermediates measured in aqueous solutions at pH 10 are recorded in Table 1B. It is seen that the standard Redox potentials measured under conditions more representitive to their actual use as hair dyes are significantly lower (less positive) than the Redox potentials measured in the organic solvent acetonitrile. Thus, these primary intermediates oxidize more readily in water than in an organic solvent as would be expected.

It is also preferable that the primary intermediates and couplers have a pKa in the range from about 3 to about 10, preferably between about 5 and about 10. The term pKa has it usual chemical definition: the negative logarithm of the acid dissociation constant, i.e., $pK_a = -\log_{10} K_a$. Thus, a pKa of 5 corresponds to an acid dissociation constant of $10^{-5}$.

TABLE 1A

Standard Redox Potentials of Dye Precursors in Acylonitrile[a]

| Dye Precursors | $E_1°$, mV | $E_2°$, mV |
|---|---|---|
| 1,4-Phenylenediamine (PPD) | 260 | 730 |
| 2,4-Diaminotoluene (TDA) | 710 | |
| 4-Aminophenol (PAP) | 120 | |
| 3-Methyl-4-Aminophenol | ~120 | |
| 1,3-Phenylene diamine | 850 | |
| 2-Methyl-4-Aminophenol (PAOC) | 750 | |
| 1,3-Dihydroxybenzene | 1,100 | |
| 1-Naphthol | 1760 | |
| N,N-dimethyl PPD | 0.25 | 1.03 |
| Diphenylamine | 0.86 | |

TABLE 1B

Oxidation Potentials of Primary Intermediates in aqueous solution at pH 10[a,b]

| Primary Intermediates | $E°$, mV |
|---|---|
| p-Phenylenediamine (PPD) | 99.6 |
| p-Aminophenol (PAP) | 67.9 |
| 3-Methyl-4-aminophenol (3M4AP) | 70.6 |
| N,N-Bis-hydroxyethyl p-phenylenediamine | 64.4 |
| p-Toluenediamine | 51.9 |

Notes to Table 1
a) Redox potentials are expressed as reduction potential (i.e., the standard potential measured for the reduction of the reactive intermediate to the dye precursor)
b) The standard Redox potential for PDP is the total or combined reduction potential for the QDI→PDP.

In one embodiment of the invention, the pH of the dye precursor mixture is adjusted such that less than 50%, preferably less than 25% and most preferably less than 10% of the molecules comprising the dye precursors, i.e., the primary intermediate and coupler, are in their anionic form when in contact with the hair during the time period before the electrical potential is applied to induce oxidation. For example, if the precursor contains both an amine and an alcohol group, the pH should be below the pKa of the hydroxyl group of the alcohol. It has been found that this pH environment leads to retention of dye precursor within the hair fiber and color resistance.

In another embodiment of the invention, the pH of the dye precursor mixture is adjusted such that more than 50%, preferably more than 75% and most preferably more than 90%, of the molecules comprising the dye precursors, i.e., the primary intermediate and coupler, are in their neutral forms when in contact with the hair during the time period before the electrical potential is applied. For example, if the precursor is an amine, the pH should be above the pKa of the conjugate acid of the amine precursor, e.g., an ammonium group. If the precursor contains both an amine and an alcohol group, the pH should be above the pKa of the conjugate acid of the amine but below the pKa of the hydroxyl group. It has been found that this pH environment can lead to higher retention of dye precursor within the fiber and better color resistance.

Couplers, such as those detailed hereinafter, are preferably used in conjunction with the oxidation dye precursors herein and are thought to interpose themselves in the colored polymers during their formation and to cause shifts in the electronic absorption spectra thereof, thereby resulting in color changes. A representative list of oxidation dye precursors (primary intermediates and couplers) suitable for use herein is found in Sagarin, "Cosmetic Science and Technology"," Interscience, Special Edition, Volume 2, pages 308 to 310 which is hereby incorporated by reference.

The typical aromatic diamines, polyhydric phenols, aminophenols, and derivatives thereof, described above as primary dye precursors can also have additional substituents on the aromatic ring, e.g. halogen, alkyl, alkyl substituted additional substituents on the amino nitrogen, on the phenolic oxygen, or on the aromatic carbon, e.g., substituted and unsubstituted alkyl and aryl groups.

The hair coloring compositions of the present invention may, in addition to the essential oxidative hair-coloring agents, optionally include non-oxidative and other dye materials. Optional non-oxidative and other dyes suitable for use in the hair coloring compositions and processes according to the present invention include semi-permanent, temporary and other dyes. Non-oxidative dyes as defined herein include the so-called 'direct action dyes', metallic dyes, metal chelate dyes, fiber reactive dyes. Numerous examples of these and other synthetic and natural materials can be found in the compendium "Chemical and Physical Behaviour of Human Hair" 3rd Edn. by Clarence Robbins (pp 250–259); 'The Chemistry and Manufacture of Cosmetics'. Volume IV. 2nd Ed. Maison G. De dyes. Various types of non-oxidative dyes are detailed in: 'Navarre at chapter 45 by G. S. Kass (pp 841–920); 'Cosmetics: Science and Technology' 2nd Edn, Vol. II Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139). The above articles are hereby incorporated by reference.

Specific hair dyes which may be included in the compositions as the primary intermediate includes: 3-methyl-p-aminophenol; 2,3-dimethyl-p-aminophenol; p-phenylene diamine, p-toluenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-di-(p-N,N-bis-(2-hydroxyethyl)-aminoanilino)-2-propanol; 2-methyl-4-dimethylaminoaniline; p-aminophenol; p-methylaminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol; 2,5-diaminotoluene; 2-dimethylamino-5-aminopyridine; -tetra-aminopyrimidine; 4,5-diamino-1-methylpyrazole; 4,5-diamino-1-hydroxyethyl pyrazole, 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 5-chloro-2,3-dihydroxypyridine; 2-hydroxyethylamino-6-methoxy-3-aminopyridine; 3,4-methylenedioxyaniline; 5,6-dihydroxyindole; 7-hydroxyindole; 5-hydroxyindole; 2-bromo-4,5-methylenedioxyphenol; 3-amino-2-methylamino-6-methoxypyridine; 2-amino-3-hydroxypyridine; 4-hydroxy-2,5,6-triaminopyrimidine, 5-hydroxyindole, 7 hydroxyindole, 5 hydroxyindoline; 7 hydroxyindoline or combinations thereof.

Preferred primary intermediates for use in the invention include: p-phenylenediamine; p-aminophenol; N,N-bis(2-hydroxyethyl)-p-phenylenediamine; 2,5-toluenediamine; 2-methyl-p-aminophenol; 3-methyl-p-aminophenol; 2,3-dimethyl-p-aminophenol,p-methylaminophenol; 4,5,-diamino-1-hydroxyethyl pyrazole, 2,4,5,6-tetrasaminopyrimidine; 4-hydroxy-2,5,6-triaminopyrimidine; and mixtures thereof.

The most preferred primary intermediates are those that generate quinone monoimine, substituted quinone monoimines, quinone dimine, substituted quinone diimine, indole imine, and substituted indole imine reactive intermediates resulting from oxidation by the electrode system. These especially preferred primary intermediates include p-phenylenediamine; p-aminophenol; 3-methyl-p-aminophenol; N,N-bis(hydroxyethyl)-p-phenylenediamine; 2,5,-toluenediamine; indoles and substituted indoles such as hydroxyindoles and mixtures thereof.

The primary intermediate is generally present in the precursor mixture at a level from about 0.005 wt % to about 10 wt %, preferably from about 0.01 to about 5 wt %, and most preferably from about 0.01 to about 4 wt %.

The coupler (or secondary intermediate) is utilized to expand the color range by reacting with the primary intermediate. These couplers work in concert with a primary intermediate, which must be present in the precursor mixture.

Specific hair dye intermediates that can be used as couplers in the present invention include: m-aminophenol; 2-methyl-1-naphthol; 1-acetoxy-2-methylnaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis (hydroxyethyl)-2,4-diaminophenetole; bis(2,4-diaminophenoxy)-1,3-propane; 1-hydroxyethyl-2,4-diaminobenzene; 2-amino-4 hydroxyethylaminoanisole; aminoethoxy-2,4-diaminobenzene; 2,4-diaminophenoxy-acetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; 2,6-bis(hydroxyethylamino)toluene; m-aminophenol; 2-hydroxy4-carbamoylmethylaminotoluene; m-carbamoylmethylaminophenol; 6-hydroxybenzomorpholine; 2-hydroxy4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol; 5-amino-4-methoxy-2-methylphenol; 1-phenyl-3-methyl-5-pyrazolone; 5-hydroxy-1,4-benzodioxane; 3,4-methylenedioxyphenol; 2,6-dihydroxy-3,4-dimethylpyridine; 3,5-diamino-2,6-dimethoxypyridine; 2,6-bis-hydroxyethoxy-3,5-diaminopyridine; 3-amino-5-hydroxy-2,6-dimethoxypyridine; 4-hydroxyindole; 6-hydroxyindole; 2-amino-3-hydroxypyridine; 2,6-diaminopyridine; 5-(3,5-diamino-2-pyridyloxy)-1,3-dihydroxypentane; 3-(3,5-amino-2-pyridyloxy)-2-hydroxypropanol; 4-hydroxyindoline; 6-hydroxyindoline; o-aminophenol or combinations thereof.

Preferred couplers for use in the invention include: o-aminophenol; resorcinol; m-aminophenol; 5-amino-2-methylphenol; 2-methyresorcinol; 1-napthol; 2-methyl-1-napthol; 2-(2,4-diamino-phenoxy)ethanol; 1-phenyl-3-methyl-5-pyrazolone; m-phenylenediamine; 4-hydroxyindole; 6-hydroxyindole; 4-chlororesorcinol; 2-chlororesorcinol; 2,6-diaminotoluene; 4-hydroxyindoline; 6-hydroxyindoline; o-aminophenol; 1phenyl-3-methyl-5-pyrazoline; 2,6-diaminopyridine; and mixtures thereof.

The most preferred couplers are o-aminophenol; 1-naphthol; 2-methylresorcinol; resorcinol; m-aminophenol; 5-amino-2-methylphenol; 2(2,4-diaminophenoxy)-ethanol; m-phenylenediamine; 1-phenyl-3-methyl-5-pyrazolone; 2,6,-diaminopyridine and mixtures thereof.

The coupler is generally present in the precursor mixture at a level from about 0.005 wt % to about 10 wt %, preferably from about 0.01 to about 5 wt %, and most preferably from about 0.01 to about 4 wt %.

The weight ratio of primary intermediate to coupler is generally in the range from about 100 to about 0.01, preferably from about 50 to about 0.05 and most preferably from about 10 to about 0.1.

It should be understood that the descriptions of primary intermediates and couplers given above are meant to implicitly include the salt forms of those dye molecules that form stable salts. For example, the hydrochloride or sulfate salts in the case of amines, and the alkali metal salts in the case of phenols.

Solubility Enhancers

Water is the preferred principal solvent, carrier or diluent for the compositions according to the present invention. As such, the compositions according to the present invention may include one or more solubility enhancers as defined above. Generally, two preferred classes of solubility enhancers are solvents and surfactant systems.

Preferred solvents are miscible with water and innocuous to the skin. Solvents suitable for use herein include $C_1$–$C_{10}$ mono- or polyhydric alcohols and their ethers, glycerine, monohydric and dihydric alcohols and their ethers. In these compounds, alcoholic residues containing 2 to 6 carbon atoms are preferred. Thus, a particularly preferred group includes ethanol, isopropanol, n-propanol, butanol, propylene glycol, ethylene glycol monoethyl ether, hexylene glycol and mixtures thereof.

The solvents may be present in the precursor mixture at a level of from about 0.1 to 20 wt %, preferably from about 0.1 to about 15 wt % and most preferably from about 0.5 to 10 wt %.

The second class of solubility enhancer useful in the present invention is surfactants.

A particularly suitable class of surfactants is cationic surfactants. One type of preferred cationic surfactant is amine based and includes alkyl amines, alkylethoxy amines, ethoxylated alkyl amines and alkyl alkanol amines. Preferred alkyl groups have 1 to about 22 carbon atoms and can have a mixture of chain lengths, e.g., methyl and hexadecyl. The term amines include primary, secondary, tertiary and quaternary amines.

A second type of preferred cationic surfactant is amidoamines and includes C12–C22 alkyl or alkylethoxy mono, di and higher (poly) amidoamines which can be ethoxylated or unethoxylated. Examples include sodium dimethylaminopropyl coco-aspartamide, cocoamidopropyl dimethylamine, olivamidopropyl dimethylamine, soyamidopropyl dimethylamine, tallowamidopropyl dimethylamine, stearamidoethyl dimethylamine and mixtures thereof.

Another preferred class of surfactant that is suitable for use as a solubility enhancer is nonionic surfactants. This class includes long chain fatty alcohols, mono, di and triglyceride and their derivatives, long chain (C12–C18) alcohol ethoxylates and mixtures thereof. Examples include: steareth 20, oleth 10, laureth 4, PEG-12 glyceryl dioleate, glycerol stearate, sorbitan oleate, PPG-9 buteth-12 and mixtures thereof.

The level of surfactants used as solubility enhancers in the dye precursor mixture can generally range from 0.1 to about 30 wt %, preferably from about 0.2% to about 20 wt % and most preferably from about 0.25 to about 15 wt %.

Both solvents and surfactants can and often are combined to achieve the desired state of solubility of the primary intermediate and coupler in the dye precursor mixture. However, it has been found that the type and level of solubility enhancer affect the ability of the oxidative dyes to absorb into the hair fibers and be retained after application of an appropriate electrical potential. Although this can be difficult to predict, the optimum type and level of solubility enhancer can be determined empirically by treating a standard hair sample under controlled conditions with a precursor mixture and developing the color with an electrode system under standardized conditions. One such test protocol is the In-Vitro Color Retention Test and is described below. As discussed below, ⓓE is the distance between two colors in the Tristimulus color space. Thus, ⓓE is the change in color of the test hair sample after treatment with the precursor solution and oxidized by means of application of a 3V direct current for a set period of time 30 min. It has been found that the level and type of solubility enhancer used in the precursor solution should be such that this mixture provides a color change, ⓓE of at least about 0.15 when measured by the In-vitro Color Retention Test described below.

pH Control Agents

The dye precursor mixture has a pH that can range from about 5 to about 11, preferably from about 7 to about 10. It is preferable to avoid an acidic pH below about 5 because the rate of electrochemical coloring decreases and also because acidic solutions tend to be damaging to the hair.

Adjustment of pH can be effected by using well known acidic or basic buffering agents used for controlling pH in the field of treating keratinous fibers, and in particular human hair.

Possible acidic pH control agents include inorganic and organic acids such as hydrochloric acid, tartaric acid, citric acid, and carboxylic or sulphonic acids such as ascorbic acid, acetic acid, adipic acid, lactic acid, sulfuric acid, formic acid, ammonium sulfate and sodium dihydrogenphosphate/phosphoric acid, disodium hydrogen phosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartrate/tartaric acid, sodium lactate/lactic acid, sodium acetate/acetic acid, disodium hydrogenphosphate/citric acid and sodium chloride/glycine/hydrochloric acid and mixtures thereof.

Still other organic acids include maleic acid, malic acid, succinic acid, glycolic acid, glutaric acid, benzoic acid, malonic acid, salicylic acid, gluconic acid, polyacrylic acid, their salts, and mixtures thereof.

Especially preferred acidic pH control agents for use in the dye precursor mixture include citric acid, lactic acid, glycolic acid, acetic acid, phosphoric acid and mixtures thereof. These materials do not have the potential of generating noxious gasses through the application of a potential by the electrode system of the present invention.

Several different basic pH control agents can be used to adjust the pH of dye precursor mixture of the present invention (both in storage and at point of use). Non-limiting examples of suitable basic buffering agents are ammonium hydroxide, urea, ethylamine, dipropylamine, triethylamine and alkanediamines such as 1,3-diaminopropane, anhydrous alkaline alkanolamines such as, mono or di- or triethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-arginine, lysine, oxylysine and histidine and alkanolamines such as dimethylaminoethanol and aminoalkylpropanediol and mixtures thereof. Also suitable for use herein are compounds that form $HCO_3^-$ by dissociation in water (hereinafter referred to as 'ion forming compounds'). Non-limiting examples of suitable ion forming compounds are $Na_2CO_3$, $NaHCO_3$, $K_2CO_3$, $(NH_4)_2CO_3$, $NH_4HCO_3$, $CaCO_3$ and $Ca(HCO_3)_2$ and mixtures thereof.

Certain alkaline buffering agents such as ammonium hydroxide and monoethanolamine (MEA), urea and the like, can also act as hair swelling agents (HSA's).

Preferred alkaline or basic pH control agents for the dye precursor compositions according to the present invention, is ammonium hydroxide, sodium hydroxide, sodium carbonate, sodium carbamate and mixtures thereof.

The level of pH control agent used in the dye precursor mixture can generally range from a value of about 0.2 wt % to about 20 wt %, preferably from about 0.5 to about 18 wt % and most preferably from 1 to about 15 wt %.

Supporting Electrolyte

The precursor mixture also preferably contains a supporting electrolyte to provide the mixture with an adequate electrical conductivity. The supporting electrolyte is preferably an electrochemically inert salt. They can comprise species present or formed by the pH control or buffering agents described above or they can be salts added in addition to these buffering agents.

Preferred additional supporting electrolytes include perchorates, sulfates, borates and their mixtures. The level of additional supporting electrolyte in the oxidative dye precursor mixture ranges from about 1 to about 25% preferably about 1% to about 15% and most preferably about 5% to about 15% by weight of the precursor mixture.

Thickeners

Thickeners may be optionally included in the oxidation hair colorant compositions of the invention. Long chain fatty alcohols having from about 11 to about 18 carbon atoms in the long fatty chain can be thickener constituents of the compositions of this invention. These alcohols can be used alone, or in admixture with each other. When included in the compositions, the alcohol is preferably present at from about 0.5 to about 10 weight percent of the composition, and more preferably at from about 2 to about 8 weight percent.

Lauryl alcohol, oleyl alcohol, myristyl alcohol, stearyl alcohol, and the like, and mixtures thereof are contemplated herein as thickeners. In addition, mixtures of natural or synthetic fatty acids having fatty chain lengths of from about 11 to about 18 carbons are also useful. Several such mixtures are available commercially, and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals.

Thickening agents suitable for use in the compositions herein may also be selected from oleic acid, cetyl alcohol, oleyl alcohol, sodium chloride, cetearyl alcohol, stearyl alcohol.

Fatty alcohols of the above discussed carbon chain lengths which are ethoxylated to contain an average of one or two moles of ethylene oxide per mole of fatty alcohol can be used in place of the fatty alcohols themselves. Examples of such useful ethoxylated fatty acids include ethylene glycol cetyl ether, polyoxyethylene (2) stearyl ether, and the like; the exemplary compounds having CTFA Dictionary names of Ceteth-1 and Steareth-2, respectively.

Particularly useful thickeners for compositions used for electrochemical coloring form conducting gels that are shear thinning yet quickly recover viscosity when the shear is removed. This allows the preferred electrode systems that are in the form of a comb or brush (i.e., that have multiple electrodes) to be passed repeatedly through the hair without the dripping of the precursor mixture. Gel forming synthetic thickeners include CARBOPOL, ACULYN 28, STRUCTURE 2001, 3001, and XL, ACROSYL, SALCARE inversion type thickeners such as SALCARE SC 91 and mixtures thereof. Preferred thickeners for use herein are ACULYN 22 (RTM), steareth-20 methacrylate copolymer; ACULYN 44 (RTM) polyurethane resin and ACUSOL 830 (RTM), acrylates copolymer that are available from Rohm and Haas, Philadelphia, Pa., USA. Additional thickening agents suitable for use herein include sodium alginate or gum arabic, or cellulose derivatives, such as methylcellulose or the sodium salt of carboxymethylcellulose or acrylic polymers.

Optional Ingredients

The dye precursor compositions of the present invention can comprise a wide range of optional ingredients. Examples of these functional classes include: mildness enhancers such as cholesterol and its derivatives, hair swelling agents, anticaking agents, antioxidants, binders, biological additives, bulking agents, chelating agents, chemical additives, colorants, cosmetic astringents, cosmetic biocides, denaturants, drug astringents, emulsifiers, film formers, fragrance components, humectants, opacifying agents, plasticizers, preservatives, propellants, reducing agents, solvents, foam boosters, hydrotropes, solubilizing agents, suspending agents (nonsurfactant), sunscreen agents, ultraviolet light absorbers, and viscosity increasing agents (aqueous and nonaqueous), and hair fiber lubricants. Examples of other functional classes of materials useful in the art include solubilizing agents, sequestrants, amino acids, hydrolyzed proteins and the like.

It may also be advantageous to include agents that condition the hair to improve combability and impart a silky/moisturized feel to the hair after it dries. Such agents include fatty long chain amines and their derivatives, silicones such as dimethicone and amodimethicone, long chain fatty alcohols, cationic conditioning polymers, and mixtures of these materials. Such conditioners can be incorporated in either the precursor mixture, or even be delivered in the aligning step (see below) as part of the aligning means as is known in the art. Conditioners can also be packaged separately when kits are employed.

Although the electrochemical method described herein is capable of dyeing the hair without the need for chemical oxidants, the dye precursor solution may also include an oxidizing agent such as hydrogen peroxide. It is preferable, however to limit the level of oxidizing agent to less than 50%, more preferably less than 25% and most preferably less than 10% of the amount required to oxidize the dye precursors present in the composition.

It should be understood that the above list of ingredients is intended to illustrate the types on materials that can be incorporated. However, it is important to select materials that do not interfere with the electrochemical oxidation of the primary intermediate or that generate noxious or unwanted by-products. A person skilled in the art should be capable of selecting appropriate material having understood the principles of the instant invention.

Electrode System

The second element of the invention is an electrode system capable of oxidizing at least one of the primary intermediates in the dye precursor mixture. Preferably at least 50%, more preferably 75% and most preferable at least 90% of the colored dye molecules that are formed, are formed electrochemically and not by chemical oxidation from either a bleach or oxygen present in the air or generated electrochemically.

In simplest terms, the electrode system is comprised of conducting electrodes that contact the precursor mixture that is on the hair, a power supply connected to these electrodes, and an insulated handle/base assembly. These components are described below. The electrode system can either be a simple disposable one-use devise or be a multi-use devise of a more robust and durable construction.

Electrodes

The electrodes are preferably inert (in an electrochemical sense) conducting wires, plates, cylinders or other shapes that are brought in contact with the hair on which has been applied the precursor mixture. When a voltage is applied to the electrodes that exceeds the net electrolytic potential, oxidation of a primary intermediate will occur at the anode (e.g., the electrode in contact with the positive end of a battery), and reduction of water to hydrogen gas will occur at the cathode.

In principle, the electrodes can be a single anode/cathode pair, e.g., two wires. However, it is preferable to have a multiplicity of anodes and cathodes and even more preferable to combine or integrate the electrodes with a hair aligning and distributing means such as a comb, a pick, a brush or a mixture of these elements. This combination allows the user to efficiently initiate the oxidation of the primary intermediate and to uniformly distribute the dye molecules on the hair. The combined element also allows a more accurate control of the location of hair coloring, which is critical for coloring visible roots, or creating highlights.

Alignment means that have at least one comb or one brush element are especially preferred. The comb is an implement of grooming dating from ancient times yet patents on various improvements continue to appear. As used here a comb element consists of strip of material on which are affixed one or more rows of teeth or tines. The comb element can be of simple construction or it can be contoured or have features that induce highlighting, for example, variable spacing or length of the teeth or wells cut into the fixing strip.

A brush element as defined herein is an aligning means that has bristles set into a handle. The handle can be rigid or flexible. The bristles can be single rigid filaments or tines, flexible fibers, or tufts of fibers. The bristles can be of uniform length or they can be of different lengths either to allow the brush element to promote highlighting effects by opening channels or different depths or to allow the brush to be contoured to conform to the shape of the head. The brush can also incorporate step features which further promote highlighting, such as is disclosed in U.S. Pat. No. 6,453,909 B1, which is hereby incorporated by reference. Further, the bristles can be distributed in rows in a planar configuration or radially distributed to form an arc.

The aligning means can also comprise a combination to the above-described elements. Combinations of brush and comb elements are well known in the art and an early example may be found in U.S. Pat. No. 660,893.

Thus, in a preferred embodiment of the electrode system of the invention, some or all of the teeth, tines, filaments, or bristles of the comb or brush elements are capable of conducting electricity and serve as electrodes when connected to the power supply. These conducting tines, filaments or bristles can be simply constructed of a conducting metal such as stainless steel, or a suitable alloy, or they can be comprised of a thin coating of a conducting metal deposited of a substrate such as plastic. In the latter case for example, the conducting coating can be gold, silver, platinum, palladium, molybdenum, tin oxide or other metal that would be suitable as an electrode. The coating can also be a conducting polymer.

Although any number of anodes and cathodes can be employed in the electrode system of the invention, it is preferable that the total surface area of the anodes is greater that the total surface area of the cathodes. Preferably the surface area of the anodes exposed to the precursor mixture on the hair should be about 1.5 and more preferably twice the total surface area of the cathodes. This can be accomplished for example by having the number of anodes (or anodic tines, teeth, filaments, or bristles) exceed the number of cathodes (or cathodic tines, teeth, filaments, or bristles). Further, the anodes can be roughened or have a high surface area porous coating applied to their surface.

The reason for having the total anode surface area exceed the total cathode surface area is related to the possible redox reactions that can occur at the cathode. As discussed above, reactive intermediates that are generated at the anode quickly migrate away from the anode towards the cathode. Most of these reactive species (i.e., free radicals) can then react quickly with primary intermediates and couplers to generate colored molecules. However, some radicals can survive in solution and reach the cathode. Since the reduction potential of many of these intermediates is more positive than the reduction potential of water in alkaline solution they can be preferentially reduced back to the primary intermediate. This wasteful reduction of reactive intermediates can be minimized by having the surface area of the anodes exceed the surface area of the cathodes. However, this has to be balanced against the current carrying capacity of the electrode system and the field strength, which decrease as the surface areas of the anodes and cathodes diverge, and average distance between anode and cathode increase. In practice, the surface area ratio is preferably between about 1.5 and about 4.

The cathodes and anodes can also be of different lengths to penetrate different depths or layers of hair and further reduce the loss of radicals by the reduction process described above.

Preferably, the electrodes should also have some resistance to polarization such that the average field strength (voltage divided by average cathode-anode distance) remains reasonably constant (90% of initial value) for at least about 5 minutes and preferably for at least about 10 minutes of continuous use. The electrodes can optionally be coated with a precious transition metal layer such as, for example, palladium, that reduces their susceptibility to polarization.

Although for cost reasons it is preferable that the electrodes have a simple construction, they can also include porous coatings with added functionality. For example, the cathode can be coated with a porous salt bridge impregnated with an electrolyte to further isolate the reactive intermediates and prevent their reduction. The electrodes can also be coated with metal oxides such as tin oxide that absorb gaseous electrolysis products. Still further, the cathode can be comprised of a self-contained standard half cell which will circumvent to reduction of water.

It is emphasized that the electrode system need not be combined with an aligning means and can have a more complicated structure. For example it can comprise a cloth mesh or plastic bonnet into which electrodes are embedded or affixed. The consumer wears the bonnet for a fixed period of time during which the electrochemical oxidation takes place.

Power Supply

The electrodes described above are connected to a power supply by means of suitable "wiring". The power supply can be any means of delivering the minimum voltage required to oxidize at least one of the primary intermediates to form a reactive species. A direct current (DC) source is preferred. The power supply can be comprised of a simple disposable battery or batteries, a rechargeable battery, or it can utilize an AC to DC converter to generate the required potential and current.

Disposable batteries include multiple-use batteries such as standard 3V (or higher) AAA, C or D alkaline cells or miniature batteries having sufficient storage for a single use.

Rechargeable batteries can also be employed and the recharger can be a part of the electrode system of can be a separate unit to which the electrode system is coupled.

It is preferable for safety and performance reasons to employ direct current. Normal AC current can be converted by means of readily available AC to DC converters that provide suitable voltage and current for use in electrochemical hair coloring, e.g., about 10 mV to about 3 V and about 10 mA to about 1.5 A respectively.

The power supply can also be a storage device that can be charged through direct mechanical action.

Handle/Base Assembly

The handle and base assembly provides an insulated means to hold the device and to affix the electrodes. The handle can comprise a compartment for the power supply (e.g., disposable or rechargeable battery) and the internal wiring that connects the power supply to the electrodes.

The handle can be constructed of any suitable insulating material such as plastic or wood. As stated above, it is preferable to integrate the electrodes with an aligning and distributing means so as to form a convenient implement to electrochemically color the hair. It may be convenient in this case to integrate the teeth, tines, filaments or bristles with the base assembly and handle to have a unitary material design, i.e., all or most of the components can be assembled in one or two steps.

The internal wiring can be in the form of true wires or can be by means of thin films of metal coated on plastic like the design used in the fabrication of integrated circuits. The handle and base assembly can also incorporate features useful in styling the hair such as a "rat-tail".

The handle and base assembly can also incorporate other electrical components such as a switch, an on-off indicator light, a means of connection to AC current through an AC to DC converter, a re-charger port, and current/voltage regulators. The handle/base assembly can also incorporate a device to convert mechanical energy to electrical energy.

The handle and base assembly may also incorporate a variable voltage adjustment feature, e.g., a rheostat that allows the consumer to more gradually develop color or to achieve different shades according to a scale or guide supplied with the implement or kit.

The handle and base assembly can also include a reservoir that simultaneously dispenses the precursor mixture and applies the required potential to electrochemically develop the color. Several types of comb and brush implements are disclosed in the art that incorporate reservoir features and these can be adapted to function with the electrochemical dyeing process described herein.

Examples of Electrode System Designs

Figure 1:
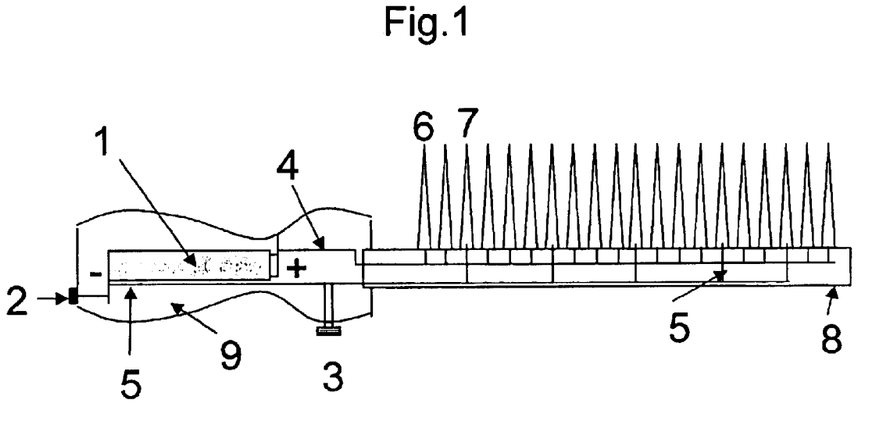
FIG. 1 is a side view schematic of an electrode system for the electrochemical dyeing of hair wherein the electrodes are combined with a comb aligning means and the power supply is a disposable battery.

FIG. 1 is a side view schematic illustration of an electrode system for the electrochemical dyeing of hair wherein the electrodes are combined with a comb hair aligning means and the power supply is a disposable battery. The anodic tines 6 are connected via a separate circuit 4 to the positive terminal of a battery 1. The fewer cathodic tines 7 are connected to the negative terminal of the battery via a separate circuit 5 which includes a switch 3 and an indicator light 2. The tines 6, 7 are affixed to an insulated base assembly 8 which is attached to an insulated handle 9.

Figure 2:
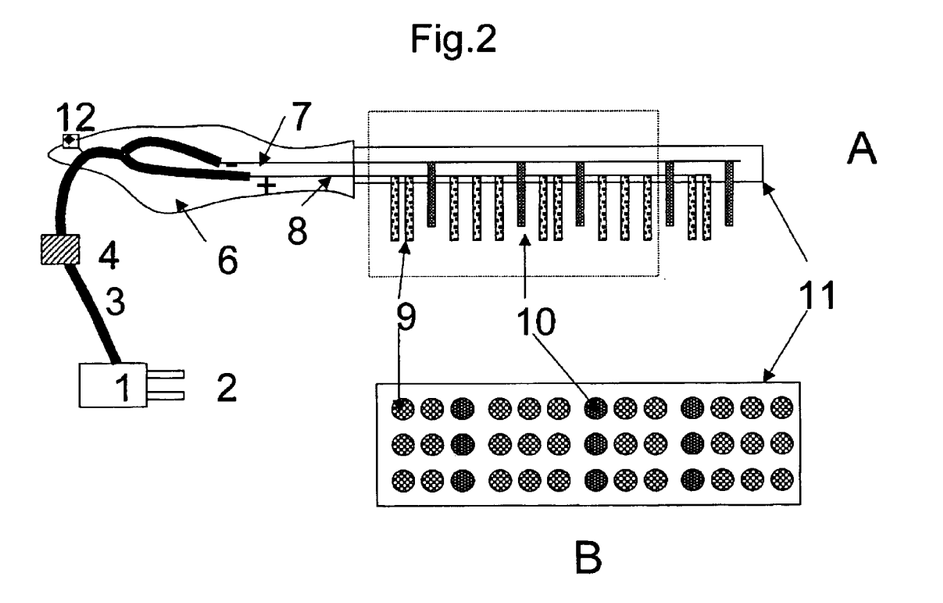
FIG. 2 is a schematic of an electrode system for the electrochemical dyeing of hair wherein the electrodes are combined with a brush aligning means and the power supply is provided from DC current by means of an AC to DC converter: A—side view; B—bottom view of section through brush head.

FIG. 2 is a schematic of an electrode system for the electrochemical dyeing of hair wherein the electrodes are combined with a brush aligning means and the power supply is provided from AC current by means of an AC to DC converter. FIG. 2A is a side view schematic. Here the multiple anode filaments 9, and fewer cathode filaments is 10, are fixed to the housing assembly 11 and are attached through separate circuits 7 and 8 connected to a DC power source. An AC to DC converter 1 has standard prongs compatible with an electrical socket 2. The wire 3 is connected to a switch 4 and an indicator light, which is attached to the handle 6. Note that in this case the cathode and anode elements are of different lengths. FIG. 2B is a bottom view of part of the housing assembly 11 showing the arrangement of combination electrode-filaments.

Applications of Methods and Compositions of the Invention

The dye precursor mixture of the present invention is first applied to hair followed by application of the electrode system that is preferably combined with a means for aligning and distributing the hair. Although the electrode system can be applied immediately, it is often preferable to allow the precursor mixture to remain in contact with the hair for a period of time ranging from about 30 seconds to about 60 minutes. Without wishing to be bound by theory, this contact time allows part of the precursors to diffuse into the hair fibers. Following the application of the electrode system and the achievement of the desired color, the hair is rinsed, and if desired a separate hair conditioner can be applied. However, hair-conditioning agents can also be incorporated in the precursor mixture obviating the need for a separate conditioning step.

The process described above is in sharp contrast to conventional permanent hair coloring methods which require that the hair be contacted with a dye precursor composition and a hair color developer composition, simultaneously or sequentially.

The electrochemical process can be used to color the entire hair. However, it also provides a convenient means to selectively color portions of the hair in a highly controlled manner. The process is especially convenient for touching up visible roots as the hair grows thus prolonging the time between complete hair coloring. Here, the precursor mixture can be applied to the root area by means of package fitted with an elongated dispensing nozzle. A specialized "touch-up" electrode system in the form of a comb is then applied to the desired areas. It should be understood that the electrode system could also include a reservoir for the precursor mixture so that the coloring process can be achieved in one step.

The process can also be used to selectively highlight the hair with different color streaks. This can be achieved ether by applying different primary intermediate/coupler mixtures or in principle by varying the voltage so as to favor different chemical reactions. Here, an electrode system that incorporates a styling feature is desirable (e.g., tines of different lengths or specialized arrangement of anodes and cathodes to favor surface dyeing or layering). Again, the styling electrode system can incorporate a reservoir feature that dispenses the precursor mixture.

Evaluation Methodology

Assessment of Initial Color and Color Change

The equipment used to measure both the initial color and color change on substrates dyed by the electrochemical coloring process described herein is a Hunter spectrophotometer. The value used to express the degree of color change induced by the combined treatment of precursor mixture and electrode system on any particular hair substrate is $\Delta E$. The term $\Delta E$, as defined herein, represents the distance in color space between two different samples, e.g., before and after treatment. $\Delta E$ is computed from the measured changes of the Tristimulus vales $\Delta L$, $\Delta a$, and $\Delta b$ values measured with the spectrophotometer by the equation:

$$\Delta E = \text{difference of color of treated and non-dyed hair: } \Delta E = \sqrt{(\Delta L^2 + \Delta a^2 + \Delta b^2)}$$

where L is a measure of lightness and darkness (color intensity), wherein L=100 is equivalent to white, and L=0 is equivalent to black. Further, 'a' is a measure of the red and green quotients (color hues) such that positive equates to red and negative equates to green, and 'b' is a measure of the yellow and blue quotients (color hues) such that positive equates to yellow and negative equates to blue.

Piedmont in-vitro Color Retention Test

A 1 gm tress Piedmont hair from International Hair Products Inc. is first treated with the aqueous dye precursor composition at a level of between 1.5 to 3 gm precursor mixture per gm of hair. The precursor is distributed over the hair surface by means of a styling brush of the type commonly employed by salon stylists. After 30 sec. to about 30 min from the completion of the application of the precursor composition, the wet hair is contacted with two electrodes having a potential difference of 3 volts that is provided by a constant direct current (DC) source for different time periods. Rinsing and drying the hair under standard conditions follows this.

The hair tresses are dried for about 30 minutes and the values of L, a, and b, are then measured and the change in color index, $\Delta E$, of the tress compared to its initial value is then computed from the above equation.

It has been found that the color change produced by oxidative dyes can depend on the chemical environment provided by the precursor mixture when it comes into contact with the hair. Precursor mixtures useful in the present invention should at least be capable of producing a color change, $\Delta E$, of at least 0.15 units when used in the above test procedure.

The resistance of the treatment to fading by for example shampoo treatment can also be measured in a similar way. After the above dye treatments, the dried hair tresses are placed in a tube containing a 10% shampoo solution and agitated for 1 hour by means of a mechanical shaker. The tresses are then rinsed and dried. The values of L, a, and b, are then measured and the change in color index, $\Delta E$, is computed and compared to their value before shampoo extraction or to the initial untreated hair as desired.

EXAMPLES

The following examples are shown as illustrations only and are not intended to limit the scope of the invention.

Example 1

Electrochemical Coloring of Hair Using 1,4-phenylene diamine (PPD) and 2-methyl-4-aminophenol (PAOC) at pH 7

This example illustrates the coloring of hair with oxidative dyes without the use of peroxide and alkaline solutions like ammonia by using an electrode system to initiate and drive the coupling reaction.

Two tresses (0.5 gm) of Piedmont hair were placed in 5 ml of an aqueous mixture whose composition is shown in Table 1A. In this case the primary intermediate is PPD and the coupler is PAOC. The pH of the mixture was 7.0.

A voltage of 3 V was applied to the precursor mixture on the hair by contacting it with two wires connected to a dry cell battery. After 30 minutes the electrodes were removed and the hair swatch was rinsed with water and allowed to dry.

The above procedure was repeated with a mixture having exactly the same composition and also for the same time but in this case the electrical leads were not connected to the battery (i.e., 0V).

The changes in color resulting from these two procedures are compared in Table 1B. It is seen that the change in color index is over twice as large for the hair samples in which a voltage was applied with a single anode-cathode pair. It is also of note that this example also illustrates that the electrochemical hair coloring method of the invention does not require either hydrogen peroxide or ammonia.

TABLE 1A

Dye precursor mixtures used in Example 1

| 1A. Dye precursor mixture Ingredients | Wt % | pH |
|---|---|---|
| 1,4-phenylene diamine (PPD) | 0.3 | 7.0 |
| 2-methyl-4-aminophenol (PAOC) | 0.35 | |
| Isopropanol | 10 | |
| Supporting electrolyte (sodium perchorate) | 2.0 | |
| Deionized water | to 100% | |

TABLE 1B

Change in color after electrochemical treatment Vs a control

| Treatment | Change in Tristimulus values relative to untreated Hair[a] | Change in Color Index, $\Delta E^a$ |
|---|---|---|
| Example 1 | | |
| Electrochemical coloring for 30 minutes @ 3 volts (single anode-cathode pair, pH = 7) | $\Delta L = -30.6$<br>$\Delta a = 13.8$<br>$\Delta b = -10.0$ | $\Delta E = 35$ |

TABLE 1B-continued

Change in color after electrochemical treatment Vs a control

| Treatment | Change in Tristimulus values relative to untreated Hair[a] | Change in Color Index, ⊕E[a] |
|---|---|---|
| Comparative Example | | |
| No current passed through solution | ⊕L = −10<br>⊕a = 8.5<br>⊕b = −6.1 | ⊕E = 14.5 |

[a]"⊕L" represents the change in color intensity, "⊕a" represents the change in the ratio of red and green hue and "⊕b" represents the change in the ratio of yellow and blue hue of the color. ⊕E is equal to the square root of the sum of the squares of ⊕L, ⊕a, and ⊕b.

Example 2

Electrochemical Coloring of Hair Using Several Oxidative Dyes at pH 10

This example illustrates the invention using another primary intermediate and coupler. The example also demonstrates that a coupler alone is not sufficient for electrochemically coloring hair in the absence of a primary intermediate.

In Example 2A–2I tresses (0.5 gm) of Piedmont hair were separately placed in 5 ml of the aqueous mixtures whose composition are shown in Table 2. The pH of all the mixtures was 10.0. A voltage indicated in the Table 2 was applied to the precursor mixture on the hair by contacting it with two wires connected to a dry cell battery. After 30 minutes the electrodes were removed and the hair tress was rinsed with water and allowed to dry. The changes in color are given in Table 2.

It is seen from Table 2 that 1,4-phenylene diamine/2-methyl-4-aminophenol and the 1,4-phenylenediamine/ Resorcinol and N,N-bis-dihydroxyethyl/1-naphthol, p-phenylene diamine primary intermediate-coupler pairs are activated albeit to varying degrees by the application of an electrical potential (compare 3V with 0V: Examples 2A Vs 2B, 2D Vs 2E, and 2G Vs 2H). However, use of the couplers by themselves are not effective in electrochemically coloring the hair—the primary intermediate must also be present, e.g., Examples 2A Vs 2C, 2D Vs 2F.

It should be noted that not all the dye pairs exhibit the same difference between the "0" current and 3 Volt color changes. Without wishing to be bound by theory, the differences are probably related to the ease of air oxidation of each dye (no doubt catalyzed by transition metal ions present in the hair), i.e., their oxidation potentials under the conditions tested. Examples 2J–2L support this conclusion. At pH 10 where 3-Methyl-4-Aminophenol oxidizes to a limited extent even in air, the differences are small. However, at pH 7 where the oxidation potential is less positive, electrochemical oxidation produces a larger relative effect.

TABLE 2

Dye precursor mixtures used in Example 2 and results

| Ingredients | Ex 2A | Ex 2B | Ex 2C | Ex 2D | Ex 2E | Ex 2F | Ex 2G | Ex 2H | Ex 2I | Ex 2J | Ex 2K | Ex 2L |
|---|---|---|---|---|---|---|---|---|---|---|---|---|
| 1,4-phenylene diamine | 0.3 | 0.3 | | 0.2 | 0.2 | | | | | | | |
| 2-methyl-4-aminophenol (p-amino-o-cresol) | 0.35 | 0.35 | 0.35 | | | | | | | 0.3 | 0.3 | 0.3 | 0.3 |
| Resorcinol | | | | 0.21 | 0.21 | 0.21 | | | | | | |
| 3-Methyl-4-Aminophenol | | | | | | | | | | 0.3 | 0.3 | 0.3 | 0.3 |
| N,N-bis-dihydroxyethyl, p-phenylene diamine | | | | | | | 0.2 | 0.2 | | | | |
| 1-napthol | | | | | | | 0.2 | 0.2 | | | | |
| NaOH to pH 10 | X | X | X | X | X | X | X | X | X | X | | |
| Applied Voltage | 3 V | 0 V | 3 V? | 3 V | 0 V | 3 V | 3 V | 0 V | 3 V | 0 V | 3 V | 0 V |
| pH | 10 | 10 | 10 | 10 | 10 | 10 | 10 | 10 | 10 | 10 | 7 | 7 |
| Change in Tristimulus values | | | | | | | | | | | | |
| ⊕L | −37.1 | −14.9 | −5.8 | −32.1 | −12.4 | −9.8 | −28.5 | −25 | −27.8 | −20.3 | −19 | −7.4 |
| ⊕a | 14.4 | 10.6 | 2.1 | 1.8 | 2.7 | 0.24 | −7.2 | −7.0 | 22.1 | 20.5 | −14.2 | −7.1 |
| ⊕b | −15 | −4.9 | −0.2 | 2.5 | −6.8 | −3.2 | −28.7 | −26.2 | −2.0 | −2.9 | 0 | 1.9 |
| Change in Color Index | | | | | | | | | | | | |
| ⊕E | 42.5 | 18.9 | 6.2 | 32.1 | 14.4 | 10.3 | 41.1 | 36.8 | 34.4 | 35.7 | 29.9 | 22.6 |

Example 3

Comparison of Direct Electrochemical Oxidation to the Possible Indirect Oxidation Through the Generation of Molecular Oxygen As discussed above, the direct oxidation of the primary intermediates useful in the instant invention, is favored over the oxidation of water to molecular oxygen. This example demonstrates that even if this were not the case, any molecular oxygen that might be generated would lead to only slight oxidation if at all.

A solution of comprising 0.1 wt % 1,4-phenylene diamine and 0.11 wt % 2-methyl-4-aminophenol, 1–5 wt % sodium perchlorate at pH 7 was prepared and divided into two parts. Both parts were initially colorless to the eye.

An electrode pair was inserted into one part and a potential of 3V was applied for 10 minutes. This mixture became highly colored.

Oxygen gas was bubbled into the other part also for 10 minutes. The solution remained colorless to the eye.

The UV-Vis absorbance at a wavelength of about 490 nm exhibited a 2.5 fold higher absorbance for the electrolyzed sample with the oxygen bubbled sample exhibiting a very shallow peak indicating little, if any, conversion of the precursors to indo dye.

This indicates that electrochemical dyeing is the direct oxidation of the dye at the anode and not the indirect oxidation by molecular oxygen as had been proposed by Larsky et al. in U.S. Pat. No. 5,472,456.

Example 4 pH Dependence of Electrochemical Hair Coloring

Tresses of Piedmont hair (5 gm) were treated with solution containing 0.3 wt % 1,4-phenylene diamine and 0.35 wt % 2-methyl-4-aminophenol adjusted to pH 7, 9 or 10 with sodium hydroxide. A potential of 3V was applied to the precursor mixture on the hair by contacting it with two wires connected to a dry cell battery. After 30 minutes the electrodes were removed and the hair swatch was rinsed with water and allowed to dry. The changes in color are given in Table 3A.

Similar experiment were carried out with 1,4-phenylene diamine/resorcinol and N,N-bis-dihydroxyethyl,p-phenylene diamine and 1-napthol buffered at to different pH values. The changes in color are given in Table 3B and Table 3C respectively.

In the case of both the 1,4-phenylene diamine/2-methylaminophenol and the 1,4-phenylene diamine/resorcinol dye precursor pairs the change in color is much greater at pH greater than or equal to 9 as compared to pH 7.

TABLE 3A

Effect of treatment pH on the electrochemical coloring of hair with 1,4-phenylene diamine/2-methyl-4-aminophenol

| Treatment pH | Change in Tristimulus values relative to untreated Hair | Change in Color Index, ①E |
|---|---|---|
| 7 | ①L = −30.6<br>①a = 13.8<br>①b = −10.0 | ①E = 35 |
| 9 | ①L = −37.8<br>①a = 15.8<br>①b = −13.1 | ①E = 43.0 |
| 10 | ①L = −37.1<br>①a = 14.4<br>①b = −15.0 | ①E = 42.6 |

TABLE 3B

Effect of treatment pH on the electrochemical coloring of hair with 1,4-phenylene diamine and resorcinol (0.3/0.35 wt % respectively)

| Treatment pH | Change in Tristimulus values relative to untreated Hair | Change in Color Index, ①E |
|---|---|---|
| 7 | ①L = −16.5<br>①a = 2.4<br>①b = −1.9 | ①E = 17.7 |
| 8 | ①L = −23.5<br>①a = 2.2<br>①b = −0.7 | ①E = 23.7 |
| 9 | ①L = −31.9<br>①a = 2.2<br>①b = −6.2 | ①E = 32.5 |

TABLE 3B-continued

Effect of treatment pH on the electrochemical coloring of hair with 1,4-phenylene diamine and resorcinol (0.3/0.35 wt % respectively)

| Treatment pH | Change in Tristimulus values relative to untreated Hair | Change in Color Index, ①E |
|---|---|---|
| 10 | ①L = −32.1<br>①a = 1.8<br>①b = −6.8 | ①E = 32.9 |

TABLE 3C

Effect of treatment pH on the electrochemical coloring of hair with N,N-bis-dihydroxyethyl, p-phenylene diamine and 1-napthol (0.2/0.2 wt % respectively)

| Treatment pH | Change in Tristimulus values relative to untreated Hair | Change in Color Index, ①E |
|---|---|---|
| 7 | ①L = −28.5<br>①a = −7.0<br>①b = −10.5 | ①E = 41.1 |
| 10 | ①L = −37.4<br>①a = −4.5<br>①b = −6.1 | ①E = 38.4 |

Example 5

Formulated Gel Compositions for Electrochemical Coloring System

This example illustrates formulated compositions for an electrochemical coloring system employing an electrically conducting gel structuring system. The compositions described in Table 4 were prepared and tested for their effectiveness in electrochemical coloring. A combination of CARBOPOL ETP 2020 (a Carbomer) and xanthan gum was employed for Example 5A while a combination of STRUCTURE XL and xanthan gum was used in Example 5B. Both compositions were effective in the in-vitro coloring of Piedmont hair when a voltage of 3 to 6 volts was applied. These structuring systems provided acceptable viscosity without interfering with the electrochemical process.

TABLE 4

Compositions for Exampl 5

| Ingredients | Example 5A Wt % | Example 5B Wt % |
|---|---|---|
| Carbopol ETP 2020 | 0.75 | |
| Structure XL | | 0.75 |
| Xanthan Gum | 0.10 | 0.10 |
| Propylene Glycol | 2.50 | 2.50 |
| Isopropanol | 2.0 | 2.0 |
| p-Amino-o-Cresol | 0.35 | 0.35 |
| p-Phenylenediamine | 0.30 | 0.30 |
| p-Aminophenol | 0.10 | 0.10 |
| Sodium perchlorate | 0.50 | 0.50 |
| Sodium bisulfite | 0.20 | 0.20 |
| EDTA | 0.10 | 0.10 |
| Isoascorbic acid | 0.10 | 0.10 |
| Fragrance | 0.02 | 0.02 |
| Sodium hydroxide | 0.50 | 0.50 |
| Water | 92.48 | 92.48 |
| Total | 100.00 | 100.00 |

Example 5
This Example Illustrates Electrochemical Hair Coloring Systems
A. Oxidative Dye Precursor Composition
Compositions of Example 5A or 5B are packaged in separate containers
B. Electrode System
Comb comprised of metal conducting tines providing a 3 volt potential and delivering a current of 75 mA to 1.5 A. Power source: and AC to DC converter or a rechargeable battery Ratio of anode to cathode surface area is 1.5.

Example 7
This Example Illustrates a Kit Comprising an Additional Instruction Sheet The invention also relates to a kit for carrying out the electrochemical hair coloring method of the invention. The kit may comprise a hair dye precursor part, an electrode system optionally coupled to an alignment and distributing means, and a post treatment solution. Each component may be in a separate container or in a dual container, as described herein. The kit may optionally comprise an integrated system that incorporates two or more of the above means to carry out the above step, e.g., an electrode system that dispenses the dye precursor mixture. The kit also contains written instructions that explain how the compositions of the invention are used. For example, "Apply precursor mixture to hair. After 10 minutes, turn on the electrochemical color-developing comb and comb the hair until the desired color is achieved. After 15 minutes rinse hair well and dry".

The consumer can admix the components of the kit according to written instructions, to obtain the aqueous reaction mixture. After treatment for a desired time with the hair dye precursor composition, the electrode system of the kit is used to align the hair, distribute the precursors and to develop the color. The excess dye may be removed, preferably with water or a conventional shampoo or a conventional conditioning shampoo.

A variety of alternative electrode systems can be provided with the kit as described above. These can range from a simple disposable or reusable comb or a brush, or a more elaborate mesh-like "bonnet" having electrodes contacting the hair.

Several types of kits can be provided. For example a starter kit comprising a precursor mixture and a reusable electrode system as well as individual kits comprising for example, refills, touch-up or streaking mixtures.

Desired change in hair color by the method of the invention is described by the mathematical formula described above. Desired change in hair color can be achieved in a number of other ways. In the first instance, the consumer can initially compare his or her hair color with desired hair color or the hair color of a sample tress. Hair dyeing by the method of the invention can be repeated until his or her hair color matches the desired hair color.

Desired hair color can also be reached by comparing hair after each treatment until it matches hair tresses taken from the consumer during a prior treatment.

Desired hair color can also be reached by testing the hair after each treatment with instruments, which measure the color of the hair. When the measurements of hair color of the treated hair reach a desired level, the treatment hair reach a desired level, the treatment can be stopped.

Indeed, reaching the desired hair color can be achieved by the use of any matching or comparison method commonly employed in the art. Further, the electrode system can incorporate a variable voltage adjustment feature that allows the consumer to gradually color the hair or to "dial-in" shades, i.e., by adjusting the voltage according to a color chart supplied with the kit.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of electrochemically dyeing hair comprising the steps of:
   i) applying to the hair an oxidative dye precursor mixture containing at least one primary intermediate having a standard Redox potential less than about 1 volt,
   ii) contacting the oxidative dye precursor mixture on the hair with an electrode system that provides sufficient voltage to electrochemically oxidize the at least one primary intermediate to produce a reactive intermediate that generates colored dye through a coupling reaction with an oxidative dye precursor present in the mixture,
   wherein the reactive intermediate is a quinone monoimine, a quinone diimine, a substituted quinone mono- a substituted quinone diimine, an indole imine, a substituted indole imine, or mixtures thereof.

2. The method according to claim 1 wherein the primary intermediate is selected from the group consisting of p-phenylenediamine, substituted p-phenylenediamine, p-aminophenol, substituted p-aminophenol, an indole, a substituted indole and mixtures thereof.

3. The method according to claim 1 wherein the oxidative dye precursor further comprises a coupler selected from the group consisting of m-substituted phenols, aminophenols and diamines, their derivatives, and mixtures thereof.

4. The method according to claim 1 wherein the oxidative dye precursor mixture has a pH in the range from about 5 to about 10.

5. The method according to claim 1 wherein the oxidative dye precursor mixture has a pH in the range from about 7 to about 10.

6. The method according to claim 1 wherein the oxidative dye precursor mixture additionally contains supporting electrolytes which are electrochemically inert salts selected from the group consisting of perchlorates, sulfates, borates, and mixtures thereof.

7. The method according to claim 1 wherein the oxidative dye precursor mixture is free of chemical oxidizing agents and/or ammonia.

8. The method according to claim 1 wherein the oxidative dye precursor mixture additionally comprises a shear thinning electrically conducting gel.

9. The method according to claim 1 wherein the electrode system comprises a plurality of anodes in contact with the precursor mixture on the hair and one or more cathodes, wherein the total surface area of the anodes is greater than the total surface area of the cathodes.

10. The method according to claim 1 wherein the electrode system further comprises an aligning and distributing means comprising at least one comb element or at least one brush element or a combination of comb and brush elements.

11. The method according to claim 1 wherein the electrode system further comprises a cloth or plastic bonnet or cap into which electrodes are embedded that can contact the hair to which the precursor mixture is applied.

12. The method according to claim 1 wherein the voltage is provided by a disposable or rechargeable battery or an electrical storage device that converts mechanical energy to electricity or an AC to DC converter.

13. The method according to claim 1 wherein the electrode system further comprises a switch, an on-off indicator, a voltage or current regulator, and a delivery means for the precursor mixture or combinations thereof.

14. The method according to claim 1 wherein the electrode system provides a regulatable voltage such that different colored dye molecules can be produced from a single dye precursor mixture depending upon the voltage selected.

15. The method according to claim 1 wherein at least 50% of the colored dye molecules that are formed are formed electrochemically and not by chemical oxidation from either a bleach or oxygen present in the air or generated electrochemically.

16. A system for electrochemically dyeing the hair comprising:
   i) an oxidative dye precursor mixture comprising at least one primary intermediate having a standard oxidation potential less than about 1V,
   ii) an electrode system that provides sufficient voltage to electrochemically oxidize at least one of the primary intermediates to produce a reactive intermediate that generates colored dye molecules through a coupling reaction with an oxidative dye precursor present in the mixture,
   wherein the reactive intermediate is a quinone monoimine, a quinone diimine, a substituted quinone mono- a substituted quinone diimine, an indole imine, a substituted indole imine, or mixtures thereof.

17. The system according to claim 16 wherein the primary intermediate is selected from the group consisting of p-phenylenediamine, substituted p-phenylenediamine, p-aminophenol, substituted p-aminophenol, an indole, a substituted indole and mixtures thereof.

18. The system according to claim 16 wherein the oxidative dye precursor mixture further comprises a coupler selected from the group consisting of m-substituted phenols, aminophenols and diamines, their derivatives, and mixtures thereof.

19. The system according to claim 16 wherein the oxidative dye precursor mixture has a pH in the range from about 5 to about 10.

20. The system according to claim 16 wherein the oxidative dye precursor mixture has a pH in the range from about 7 to about 10.

21. The system according to claim 16 wherein the oxidative dye precursor mixture additionally contains salts selected from the group consisting of perchlorates, sulfates, borates, and mixtures thereof.

22. The system according to claim 16 wherein the oxidative dye precursor mixture is free of chemical oxidizing agents and/or ammonia.

23. The system according to claim 16 wherein the electrode system comprises a plurality of anodes in contact with the precursor mixture on the hair and one or more cathodes, wherein the total surface area of the anodes is greater than the total surface area of the one or more cathodes.

24. The system according to claim 16 wherein the electrode system is further comprised of an aligning and distributing means comprising at least one comb element or one brush element or a combination of comb and brush elements.

25. The system according to claim 16 wherein the electrode system further comprises a cloth or plastic bonnet or cap into which electrodes are embedded that can contact the hair to which the precursor mixture is applied.

26. The system according to claim 16 wherein the voltage is provided by a disposable or rechargeable battery, a storage device that converts mechanical energy to electrical energy or an AC to DC converter.

27. The system according to claim 16 wherein the electrode system further comprises a switch, an on-off indicator, a voltage or current regulator, and a delivery means for the precursor mixture or combinations thereof.

28. The system according to claim 16 wherein the electrode system provides a regulatable voltage such that different colored dye molecules can be produced from a single dye precursor mixture depending upon the voltage selected.

29. The system according to claim 16 additionally including written instructions to first apply the oxidative dye precursor mixture to the hair, and after a period of time ranging from about 0.5 minutes to 45 min, apply the electrode system and allow it to contact the hair for a period of time ranging from about 30 seconds to about 30 minutes.

* * * * *